(12) United States Patent
Greenwood

(10) Patent No.: US 6,877,375 B2
(45) Date of Patent: Apr. 12, 2005

(54) SYSTEM AND TECHNIQUE FOR CHARACTERIZING FLUIDS USING ULTRASONIC DIFFRACTION GRATING SPECTROSCOPY

(75) Inventor: Margaret S. Greenwood, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 10/430,474

(22) Filed: May 6, 2003

(65) Prior Publication Data

US 2004/0031322 A1 Feb. 19, 2004

Related U.S. Application Data

(60) Provisional application No. 60/467,878, filed on May 5, 2003, and provisional application No. 60/378,530, filed on May 6, 2002.

(51) Int. Cl.[7] .............................................. G01N 29/02
(52) U.S. Cl. ........................... 73/597; 73/24.05; 73/642; 73/861.25
(58) Field of Search ......................... 73/597, 602, 642, 73/644, 24.01, 24.05, 24.06, 30.01, 31.05, 32 A, 54.41, 61.79, 64.53, 861.25

(56) References Cited

U.S. PATENT DOCUMENTS

| | | | |
|---|---|---|---|
| 4,509,360 A | * | 4/1985 | Erwin et al. ............... 73/61.75 |
| 4,527,420 A | | 7/1985 | Foote |
| 4,571,693 A | | 2/1986 | Birchak et al. |
| 4,735,097 A | | 4/1988 | Lynnworth |
| 4,991,124 A | | 2/1991 | Kline |
| 5,216,312 A | * | 6/1993 | Baer et al. .............. 310/313 D |

(Continued)

FOREIGN PATENT DOCUMENTS

EP 0477418 4/1996

OTHER PUBLICATIONS

Bridge, B and Tahir, Z. A Study of Ominidirectional Scattering of 4–30 MHz Ultrasound From Periodically Rough-Machined Aluminium Surfaces (Part 1). British Journal of NDT, vol. 31. No. 1, Jan. 1989.

DeBilly, M. and Quentin G. Measurement of the periodicity of internal surfaces by ultrasonic testing. J. Phys. D: Appl. Phys., 15 (1982) 1835–1841.

Jungman, Alain and Adler, Laszlo. Ultrasonic anomalies in the spectrum of acoustic waves diffracted by periodic interfaces. J. Appl. Phys. 53(7), Jul. 1982, pp. 4673–4680.

Primary Examiner—Hezron Williams
Assistant Examiner—Jacques M. Saint-Surin
(74) Attorney, Agent, or Firm—Woodard, Emhardt, Moriarty, McNett & Henry LLP

(57) ABSTRACT

A system for determining a property of a fluid based on ultrasonic diffraction grating spectroscopy includes a diffraction grating on a solid in contact with the fluid. An interrogation device delivers ultrasound through the solid and a captures a reflection spectrum from the diffraction grating. The reflection spectrum including a diffraction order equal to zero exhibits a peak whose location is used to determine speed of sound in the fluid. A separate measurement of the acoustic impedance is combined with the determined speed of sound to yield a measure of fluid density. A system for determining acoustic impedance includes an ultrasonic transducer on a first surface of a solid member, and an opposed second surface of the member is in contact with a fluid to be monitored. A longitudinal ultrasonic pulse is delivered through the solid member, and a multiplicity of pulse echoes caused by reflections of the ultrasonic pulse between the solid-fluid interface and the transducer-solid interface are detected. The decay rate of the detected echo amplitude as a function of echo number is used to determine acoustic impedance.

26 Claims, 11 Drawing Sheets

U.S. PATENT DOCUMENTS

| | | |
|---|---|---|
| 5,321,331 A | 6/1994 | Baer et al. |
| 5,351,560 A | 10/1994 | Russwurm |
| 5,365,778 A | 11/1994 | Sheen et al. |
| 5,396,325 A | 3/1995 | Carome et al. |
| 5,488,953 A | 2/1996 | Vilkomerson |
| 5,502,560 A | 3/1996 | Anderson et al. |
| 5,540,230 A | 7/1996 | Vilkomerson |
| 5,610,708 A | 3/1997 | Anderson et al. |
| 5,640,234 A | 6/1997 | Roth et al. |
| 5,708,191 A | 1/1998 | Greenwood et al. |
| 5,760,894 A | 6/1998 | Mersch |
| 5,886,250 A | 3/1999 | Greenwood et al. |
| 5,925,878 A | 7/1999 | Challener |
| 6,082,180 A | 7/2000 | Greenwood |
| 6,082,181 A | 7/2000 | Greenwood |
| 6,093,536 A | 7/2000 | Drake et al. |
| 6,216,538 B1 * | 4/2001 | Yasuda et al. ............. 73/570.5 |
| 6,218,194 B1 | 4/2001 | Lyndin et al. |
| RE37,473 E | 12/2001 | Challener |
| 6,763,698 B2 * | 7/2004 | Greenwood ................ 73/30.01 |

* cited by examiner

SYSTEM AND TECHNIQUE FOR CHARACTERIZING FLUIDS USING ULTRASONIC DIFFRACTION GRATING SPECTROSCOPY

RELATED APPLICATION DATA

The present application claims the benefit of commonly owned U.S. Provisional Application Ser. No. 60/378,530 filed May 6, 2002 and commonly owned U.S. Provisional Application Ser. No. 60/467,878 filed May 5, 2003 and titled Characterization of Fluids and Slurries Using Ultrasonic Diffraction Grating Spectroscopy, the disclosures of which are hereby incorporated by reference. The present application is related to commonly owned U.S. application Ser. No. 10/099,412 filed Mar. 15, 2002 and titled Self Calibrating System and Technique for Ultrasonic Determination of Fluid Properties, the disclosure of which is hereby incorporated by reference.

GOVERNMENT RIGHTS

This invention was made with Government support under Contract Number DE-AC0676RLO1830 awarded by the U.S. Department of Energy. The Government has certain rights in the invention.

BACKGROUND

The present invention relates to fluid analysis and more particularly, but not exclusively, relates to the determination of fluid properties by detecting ultrasound reflected from a diffraction grating.

Fluids are encountered in a wide variety of industrial applications, and there is a continual need to determine properties of those fluids. Ultrasound based sensors have been developed for a variety of industrial applications, but there continues to be a need to develop improved sensors and sensor techniques for determining fluid properties. In particular there is a need for sensing systems and techniques that are accurate, reliable, cost effective and can be implemented in a wide variety of industrial applications. The present invention is addressed to these needs and provides novel systems and techniques for determining fluid properties utilizing ultrasonic diffraction grating spectroscopy.

DETAILED DESCRIPTION

Figure 1:
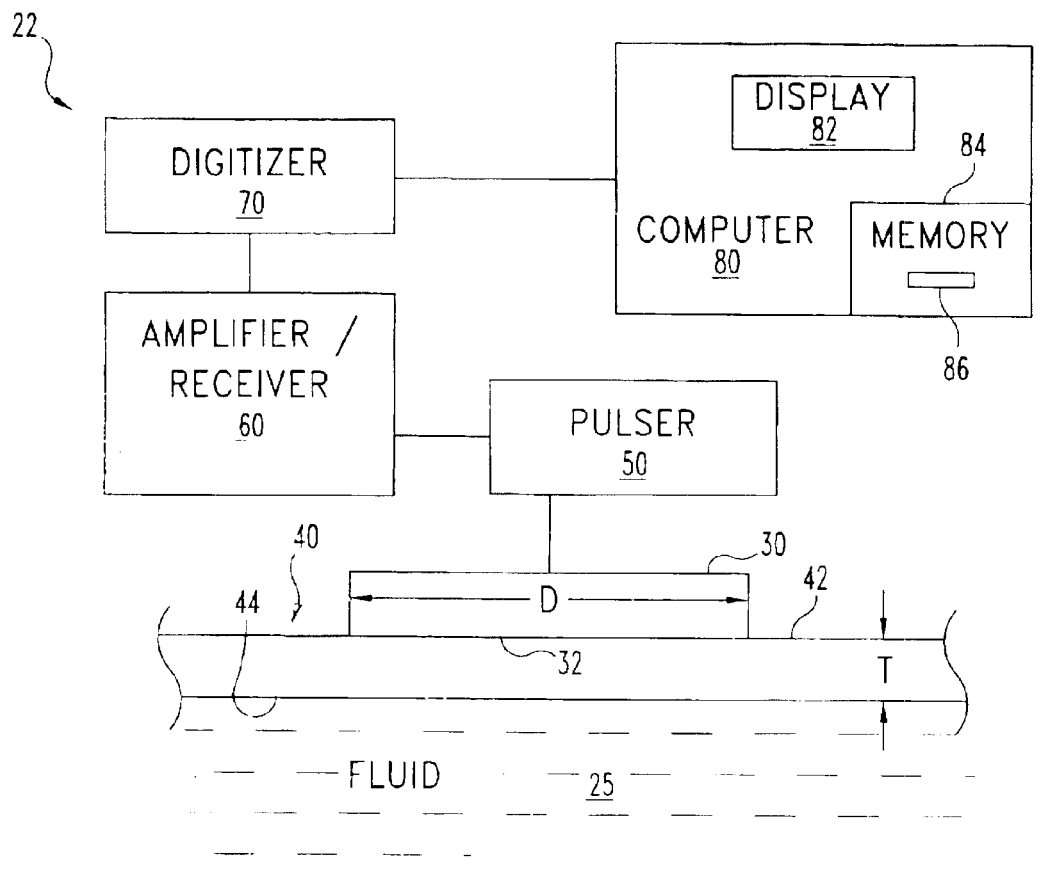
FIG. 1 is a diagrammatic view of a system for determining fluid properties via multiple reflections from a fluid-solid interface.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

In one aspect, the present invention provides a sensor for determining a property of a fluid utilizing ultrasonic diffraction grating spectroscopy. Briefly, this technique involves a diffraction grating formed on a solid that is placed in contact with a fluid. In one application, ultrasound is transmitted through the solid at an angle of incidence and a reflection of the ultrasound from the diffraction grating is collected. The reflected ultrasound exhibits a frequency dependent response that can be correlated with properties of the fluid in contact with the diffraction grating. For example, a critical frequency has been found that manifests as an identifiable peak in a plot of amplitude versus frequency for the reflected ultrasound corresponding to zero order diffraction. The location of this peak, i.e. the frequency value, has been found to correlate with acoustic velocity (i.e. speed of sound) in the fluid in both a qualitative and quantitative manner.

Turning first to FIGS. 10–13, system 400 includes a member 410 comprised of solid material having a diffraction grating 450 formed on a face thereof and positioned in contact with a fluid 420. A send transducer 430 is acoustically coupled to the solid member 410 and is configured to direct ultrasound through the member 410 and onto the diffraction grating 450 at an angle of incidence θ measured relative to a normal 460 of the grating 450. A receive transducer is acoustically coupled to the member 410 and receives ultrasound which reflects from the grating 450. As explained more fully below, the reflection spectrum from the grating 450 exhibits spatial and frequency dependence that can be correlated to properties of the fluid 420. In the schematic illustration of FIG. 10, the receive transducer 440 is positioned to receive the zero order reflection (designated m=0) which occurs at an angle of reflection θ equal to the angle of incidence θ regardless of frequency. In other variations, the receiver transducer 440 is positioned opposite the send transducer 430 relative to the normal 460 but at an angle either greater than or less than the angle of incidence θ. In still other variations, the angle θ is zero and a single transducer functions as both the send and receive transducers.

Figure 12:
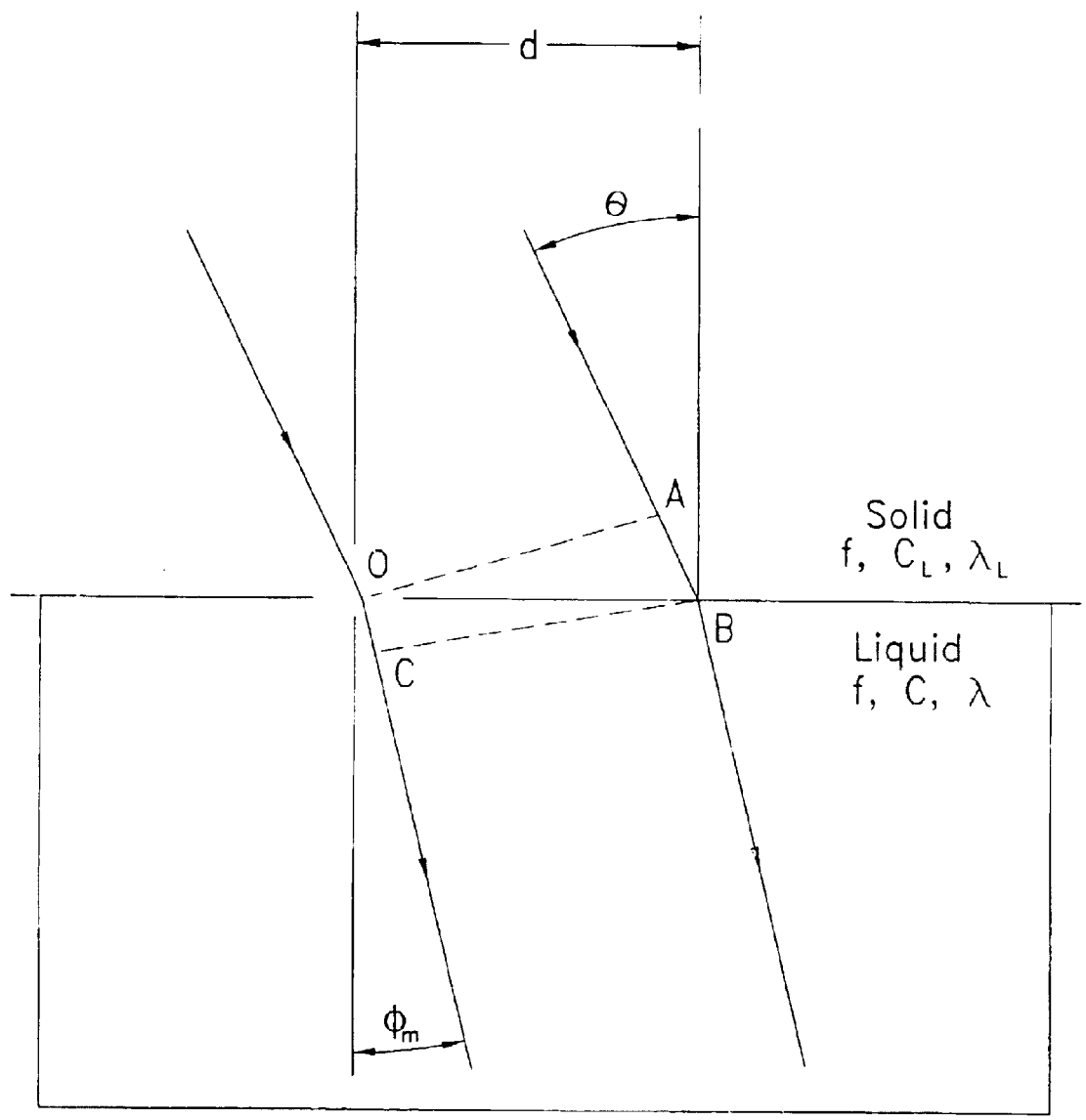
FIG. 12 is a schematic illustration of an ultrasonic beam incident on a diffraction grating.
Figure 13:
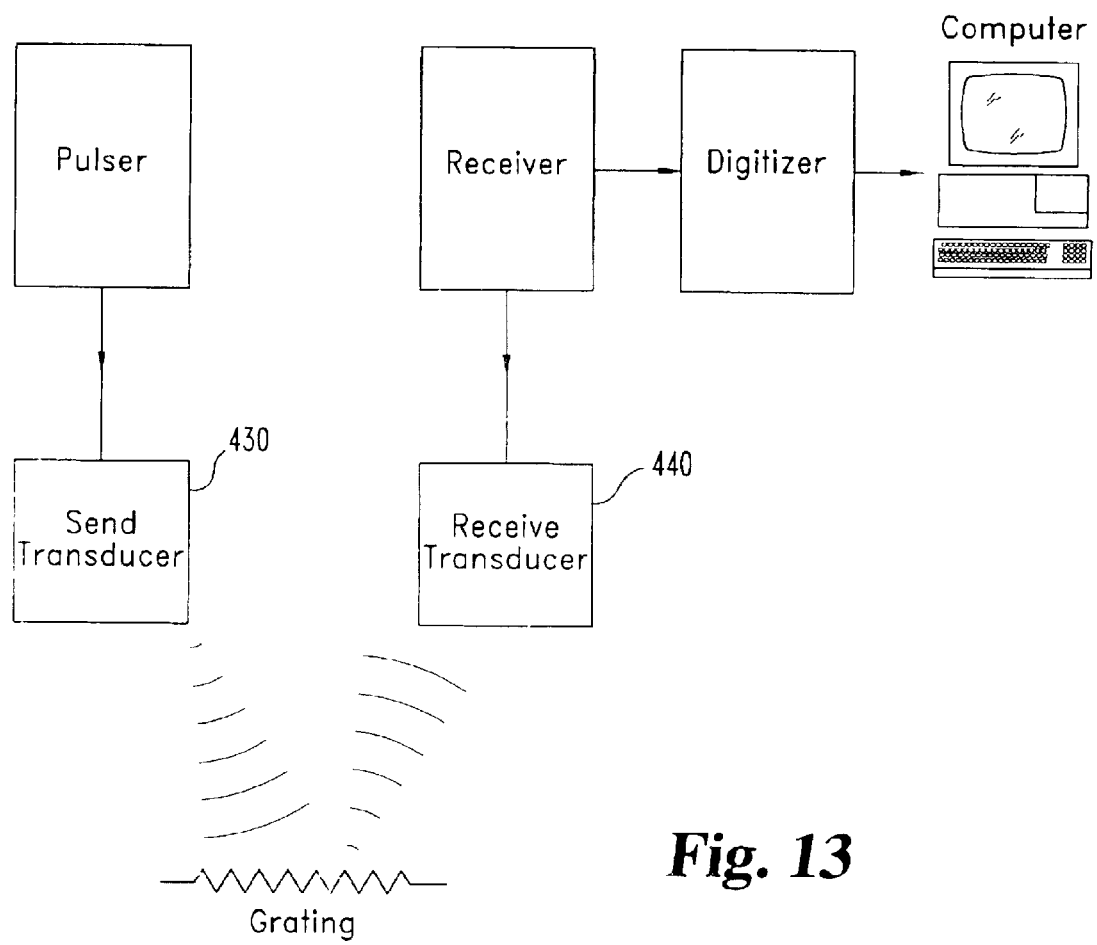
FIG. 13 is a schematic illustration of a system for performing ultrasonic diffraction grating spectroscopy.

FIG. 12 shows an ultrasonic beam of frequency f traveling through a solid, and striking a grating-liquid interface at an incident angle θ. As a result of constructive interference, a refracted beam in the liquid is produced at angle $\phi_m$. The grating period is d and is conventionally defined as the distance between adjacent grooves in the ultrasonic diffraction grating. (For simplicity, the grooves are shown schematically in FIG. 12 as "slits" though it is understood that a grating can take any periodic form, for example grooves of uniform shape, such as triangular, square, or serpentine) In the solid, the speed of a longitudinal sound wave is $c_L$ and the wavelength is $\lambda_1$. In the liquid the corresponding speed of sound is c and the wavelength is λ. Constructive interference occurs when:

$$\frac{OC}{\lambda} - \frac{AB}{\lambda_1} = m \quad (9)$$

$$\frac{df\sin\varphi_m}{c} - \frac{df\sin\theta}{c_L} = m$$

where m is zero or a positive or negative integer. When m=0, Snell's Law is obtained:

$$\frac{\sin\varphi_0}{c} = \frac{\sin\theta}{c_L} \quad (10)$$

Using the results of Eq. (10), Eq. (9) becomes $$\sin\varphi_m - \sin\varphi_0 = \frac{mc}{fd} \quad (11)$$

Eq. (11) is the so-called grating equation. When m=+1, Eq. (11) determines the angle $\phi_m$. Table 1 shows the frequency required to place the transmitted longitudinal wave at angle $\phi_m$ for an exemplary stainless steel-water interface and a grating period (d) of 300 μm.

| Order m | Frequency (MHz) | Angle $\phi_m$ (degrees) |
|---|---|---|
| 0 | Any value | 7.35 |
| 1 | 6.35 | 65 |
| 1 | 6.10 | 70 |
| 1 | 5.90 | 70 |
| 1 | 5.90 | 75 |
| 1 | 5.75 | 80 |
| 1 | 5.70 | 84 |
| 1 | 5.67 | 90 |

Note that as the frequency decreases, the angle $\phi_1$ increases. When the frequency is 5.67 MHz, the angle $\phi_1$ reaches 90°,
which is termed a critical frequency $F_{CR}$. Setting $\phi_1$=90° and rearranging Eq. (11) yields an expression for this critical frequency ($F_{CR}$):

$$F_{CR} = \frac{c}{d(1-\sin\varphi_0)} \quad (12)$$

Solving Eq. (10) for sin $\phi_0$ and substituting into Eq. (12) yields an expression for the critical frequency $F_{CR}$ as a function of d, c, $c_L$ and θ:

$$F_{CR}=c/\{d[1-(c/c_L)\sin\theta]\} \quad (13)$$

Accordingly, by fixing the grating period (d), the angle of incidence (θ), and the material of the solid member 410 ($c_L$), Eq. (13) yields a means to determine speed of sound in the fluid 420 based on an identification of the critical frequency $F_{CR}$.

The significance of the critical frequency $F_{CR}$ is that it is at this frequency that the m=1 transmitted wave transforms from a traveling wave and becomes evanescent. This means that it becomes an exponentially decaying wave in the fluid 420. In order to conserve energy, the energy of the m=0 traveling wave must be redistributed in some fashion as it becomes evanescent around the critical frequency $F_{CR}$. It has been found that at least a portion of this energy is at least initially redistributed to several of the other waves, including the specularly reflected signal (the m=0 reflected wave), and that this energy redistribution can be detected as an increase in amplitude of the respective signal and used to identify the critical frequency $F_{CR}$. As described above, identification of the critical frequency $F_{CR}$ leads to a determination of a value for c in Eq. (13). A similar phenomena has been observed utilizing polarized light incident on a diffraction grating, as described in U.S. Pat. No. 5,502,560 to Anderson, which is hereby incorporated by reference.

While it has also been found that, in certain circumstances, a significant portion of the energy of the m=1 transmitted wave is ultimately transferred to the m=0 transmitted wave, thereby permitting determination of the critical frequency via direct observation of the transmitted m=0 wave, there is an advantage in observing a wave reflected from the grating 450. Observation of a reflected wave permits construction of a one-sided sensor that does not require direct detection of ultrasound that has been transmitted through the fluid 420.

Accordingly, in one aspect the invention provides a sensor wherein a pulser (see FIG. 13) excites a send transducer 430 on the solid side of a diffraction grating at a solid-fluid interface. A suitable excitation is a tone burst signal at a preselected frequency. A receive transducer 440 receives a reflection from the grating 440. The response at the receive transducer 440 is passed through a receiver and digitizer and to a computer. The frequency is then incremented and the process repeated until a desired spectrum of amplitude versus frequency is obtained. The computer corrects the amplitude to account for any variation in receiver gain and for variations attributable to the frequency dependence of the transducers. From the spectrum, the computer applies a peak picking algorithm to identify the frequency corresponding to a relevant peak in the amplitude values. A suitable algorithm is to select an appropriate frequency window (for example guided by an expected range for the critical frequency calculated from Eq. 13 based on an expected range for speed of sound in the fluid 420) and to select the frequency corresponding to the largest detected amplitude in that window. The identified frequency is than compared to a calibration database or Eq. 13 is used to determine speed of sound in the fluid 420 based on the known parameters of the system.

The transducers 430, 440 are preferably wide bandwidth transducer so as to allow a large frequency sweep, for example one or more of transducers 430, 440 having a bandwidth, measured as the full width at half maximum, at least about equal to 50% of the center frequency, more preferably at least about 60–70%. Suitable transducers have piezoelectric transducer elements and are commercially available from a variety of manufacturers, for example Xactex Corp in Pasco, Wash. Alternatively or in addition, multiple transducers of varying center frequencies can be used to collect the desired frequency spectrum.

It has been found that the detected peaks have a finite width (see e.g. FIGS. 14–16), suggesting that the evanescent transition effectively occurs over a range of frequencies. The width of the peak has been found to increases as the number of grooves of the grating incident with the ultrasound decreases. In other words, narrower or sharper peaks are observed when a greater number of grooves are illuminated with ultrasound. Accordingly, the ability to accurately resolve the frequency value corresponding to the peak, the value used to correlate with speed of sound in the fluid as described above, increases with increasing number of grooves illuminated. The number of grooves illuminated is related to the relative size of the operational face of transducer 430 and the angle of incidence θ, with a larger face providing a beam of greater cross sectional area and a larger angle θ providing greater cross sectional area of illumination. In one aspect at least about 20 grooves of grating 450 are illuminated. In other aspects at least 30–50 are illuminated.

However, it may not be practical to have a face of transducer 430 being too large, because it is advantageous to have the distance $D_S$ between the transducer 430 and the grating 450 sufficient to locate the grating 450 in the far field of the transducer 450. The distance from the transducer face to the value of the near field (calculated below) is characterized by regions of constructive and destructive interference. When the distance is greater than the near field distance, the ultrasound is fairly uniform, generally lacking such interference effects. The face of the diffraction grating should be in the far field of the send transducer 430. The near field length (Nf) for an ultrasonic transducer can be approximated by equation (8)

$$Nf=0.25D^2/\lambda \qquad (8)$$

where λ is the wavelength of the ultrasound in the medium (equal to local speed of sound divided by the frequency) and D is a dimension of the operational face of the transducer. For circular transducers, D will be the diameter of the face whereas for rectangular transducers D can be either dimension of the rectangle. For purposes of locating the beginning of the far field and the location of the send transducer 430, the smaller dimension of a rectangle is chosen. Accordingly, in one aspect, the distance $D_S$ is selected to be at least about equal to the beginning of the far field, for example in the range of 0.9 to 1.25 of the Nf according to Eq. 8 with the smaller dimension of the transducer face used for D.

The selection of the distance DR between the receive transducer 440 and the grating 450 is independent of the near field and can be chosen to be less than $D_S$, for example about 0.25 to 0.75 $D_S$, so as to minimize the attenuation of the reflected signal as it travels through the solid 410.

The selection of the grating spacing and the configuration of the grating is determined by calculating the critical frequency using Eq. 12, using a known velocity of sound for illustration of the principle or using an approximate speed for the fluids to be encountered. The choice of grating spacing and transducer frequency are related using Eq. 12. Eq. 12 also shows that, for two slightly different fluids (i.e., slightly different concentration of the sugar water solutions presented below) the critical frequency values are more widely separated when using a smaller grating spacing. That is, the sensitivity of the velocity measurement is increased by using a smaller grating spacing.

In order to be effective, the material of member 410 needs to be able to support formation of the grating and be compatible with and preferably withstand prolonged contact with the fluid 420. A wide range of material may meet one or more of these objectives such as plastics, ceramics, and metals such as stainless steel or aluminum. Preferably, though not essentially member 410 is a unitary structure providing substantially continuous material along the acoustic paths between the send transducer 430 and the grating 450 and between the grating 450 and the receive transducer 440.

The selection of the angle of incidence θ depends on the material of member 410 and the grating spacing, but will typically range between about 15° and 60°, for example between 25° and 50°, such as about 30°. For some choice of the grating material, it may be possible to use a beam that strikes the grating perpendicularly and monitor the reflection in a pulse-echo mode using only one transducer.

Observation of a peak at the critical frequency involves a balance between the strength of the reflected m=0 signal and the strength of the m=1 transmitted longitudinal wave that becomes evanescent. For example, if the m=0 reflected wave is very large and the m=1 transmitted wave is small, it may not be possible to detect a small change when the m=1 wave becomes evanescent and a portion of its energy is transferred to the m=0 reflected wave. Particularly when observing the m=0 reflected signal, improved detection ability can be achieved when parameters are selected to decrease the relative amount of ultrasound that is reflected from the grating 450 in the m=0 wave. Increasing the angle of incidence θ is one mechanism for decreasing the relative amount of reflection, while at the same time, increasing the amount of ultrasound in the transmitted m=1 wave (that will become evanescent and must be transferred to other modes).

An exemplary embodiment of the present invention was constructed and used to evaluate the speed of sound of sugar water solutions. As described more fully in commonly owned U.S. Provisional Application Ser. No. 60/467,878 filed May 5, 2003 and titled Characterization of Fluids and Slurries Using Ultrasonic Diffraction Grating Spectroscopy, 5 Mhz square transducers, 1.27 cm on a side, having a bandwidth of 50% of the center frequency at half maximum were positioned at an angle θ of 30° with respect to the normal as both the send and receiver transducers 430, 440. A 5.08 cm diameter half cylinder of stainless steel provided the diffraction grating with a grating spacing of 300 μm with a 120° included angle. A fluid path provided the acoustic communication between the transducers 430, 440 and the half cylinder, which had flat surfaces machined at the appropriate 30° angles. The face of the send transducer was a distance of about 11.2 cm from the center of the grating, ensuring that the ultrasound was in the far field when it reached the grating surface, and the receive transducer face was about 5.7 cm from the grating.

Figure 14:
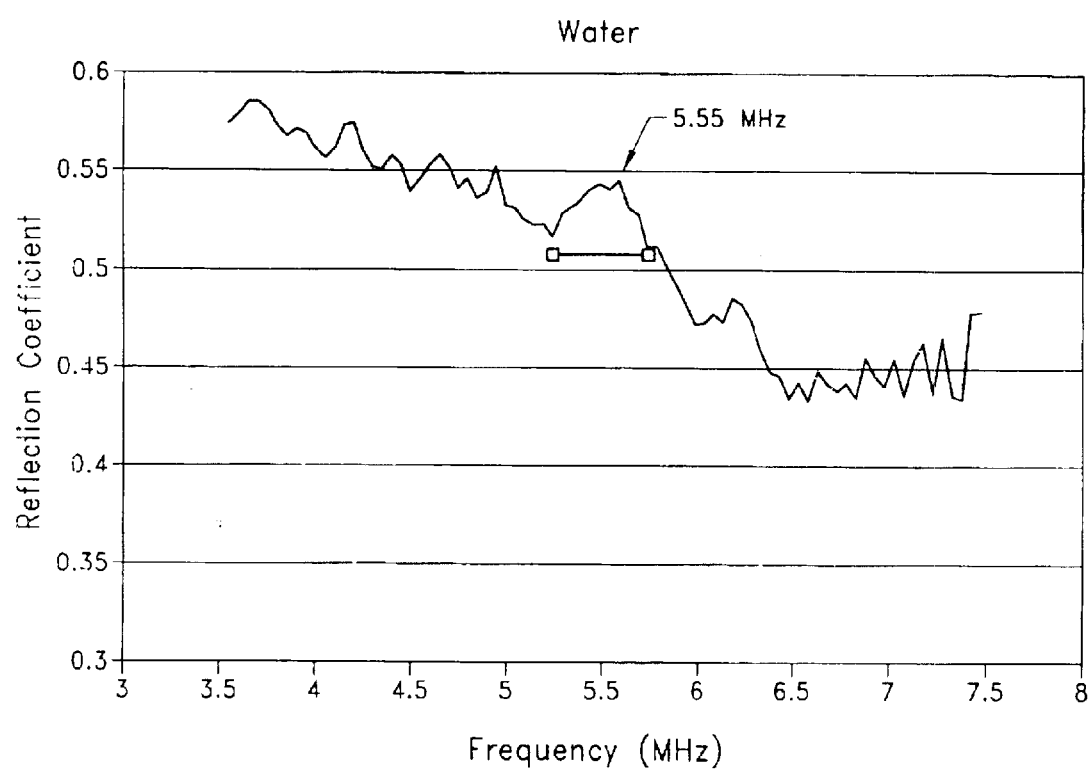
FIG. 14 is a plot of reflection coefficient as a function of frequency for the zero order diffraction collected with an exemplary embodiment as described where the fluid is water.
Figure 15:
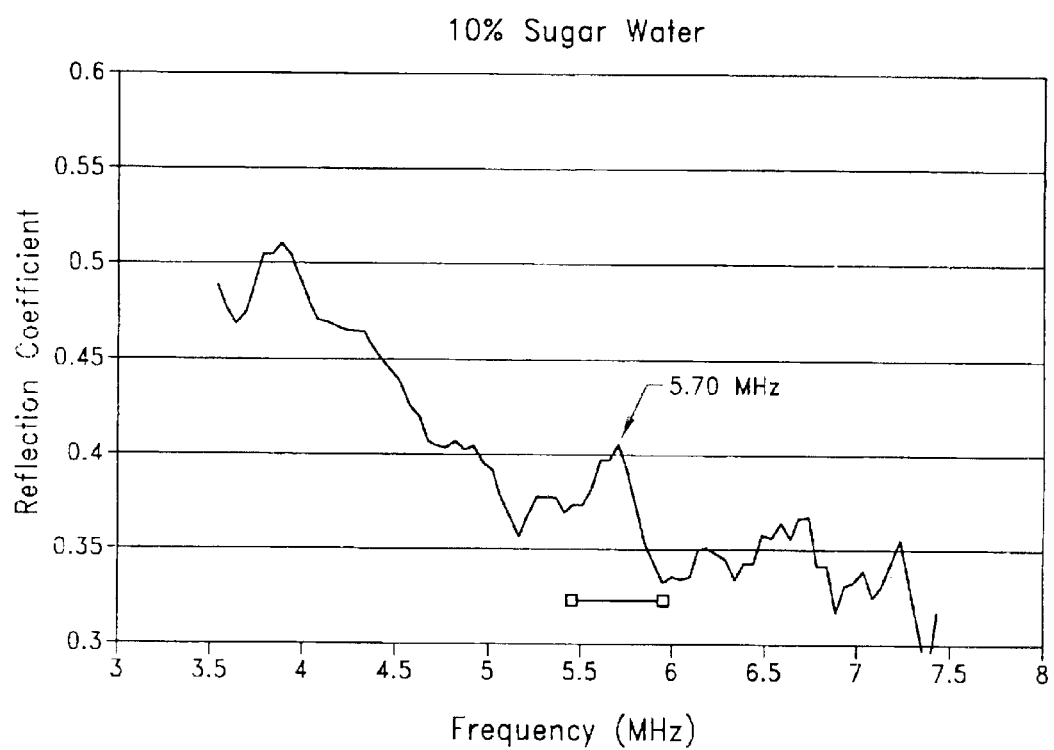
FIG. 15 is a plot of reflection coefficient as a function of frequency for the zero order diffraction collected with an exemplary embodiment as described where the fluid is 10% sugar water.
Figure 16:
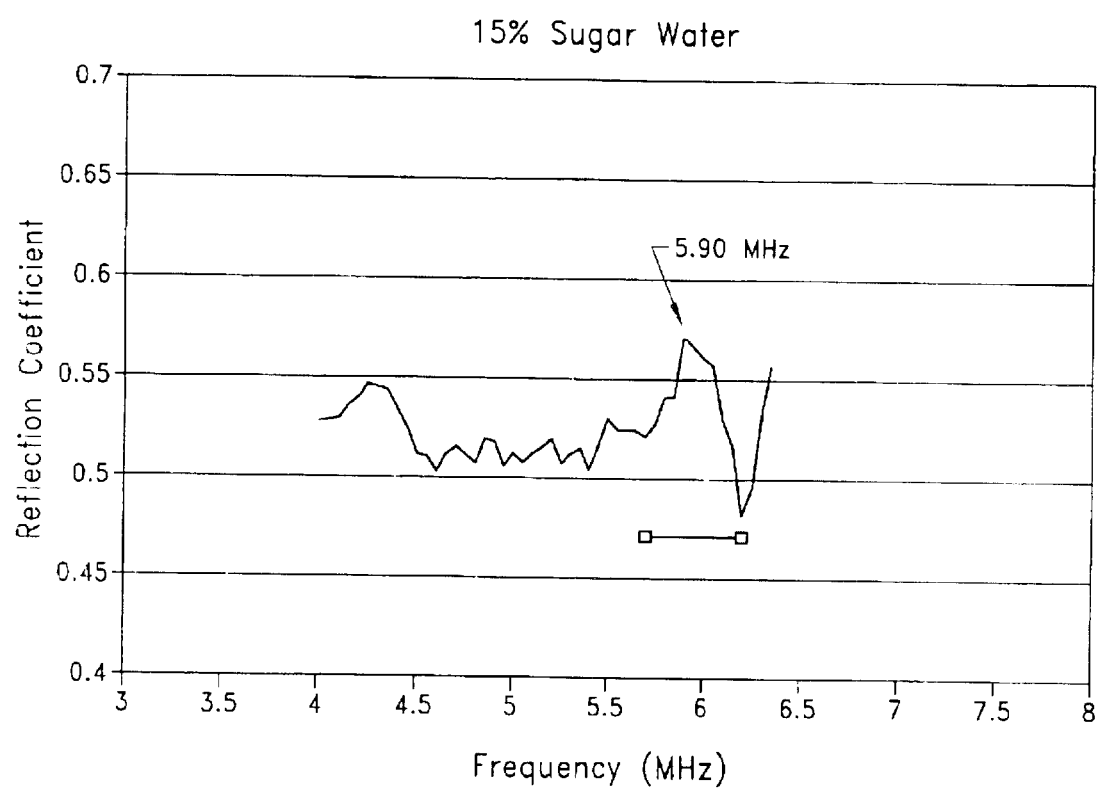
FIG. 16 is a plot of reflection coefficient as a function of frequency for the zero order diffraction collected with an exemplary embodiment as described where the fluid is 15% sugar water.

Exemplary data from a scan over frequency is present in FIGS. 14–16 where the fluid 420 is water (FIG. 14), 10% sugar water (FIG. 15), and 15% sugar water (FIG. 16). Data were obtained for the "blank" that had the same dimensions as the stainless steel block providing the grating, but with a smooth face in place of a grating. To account for variations in the transducer response over frequency, the following calculation was carried out over the frequency range:

$$\frac{\text{Amplitude for grating at a given frequency}}{\text{Amplitude for blank at a given frequency}} \quad (14)$$

That is, at each frequency, the amplitude for the grating was divided by the amplitude for the blank.

The reflection coefficients can be determined from measurements with the grating and blank. Because a transducer measures the pressure of an ultrasonic wave (not the intensity), the voltage is proportional to the pressure reflection coefficient. For a flat surface the formulation of reflection and transmission coefficient is well known and is given in Appendix A to the above referenced Provisional filed May 5, 2003. Using this formulation, the reflection coefficients for the blank immersed in various liquids were calculated. Eq. (14) is modified by multiplying by the (pressure) reflection coefficients for the blank to yield:

$$RCgrating = \frac{(Vgrating)(RCblank)}{Vblank} \quad (15)$$

where Vgrating is the voltage response for the grating, Vblank is the corresponding voltage response for the blank, and RCblank is the calculated reflection coefficient for the blank. The values for RCgrating are plotted in FIGS. 14–16.

Data below about 4.5 MHz and above about 6.7 MHz in FIGS. 14–16 is considered noisy and unreliable. Nonetheless the location of the indicated peak corresponds well with the predicted critical frequency values both qualitatively and quantitatively.

The amplitude of the peak at the critical frequency also is potentially a mechanism for determining fluid properties. For example, it is believed that the amplitude of the peak is related to the properties of the fluid and will show dependence on the particle size when the fluid is a slurry. For example, without intending to be bound by any theory, it is expected that as the m=1 transmitted wave becomes evanescent near the critical frequency, a portion of the energy will be scattered and absorbed by the particles in the slurry and will influence the relative amount of energy transferred to, and thus the amplitude of, the m=0 reflected wave. Accordingly, as between two slurries, the change in peak amplitude is expected to indicate a change in particles size.

Having determined speed of sound in the liquid, additional properties can be determined as would occur to those of skill in the art. In one aspect, speed of sound determined in accordance with the present disclosure is combined with a measured acoustic impedance value to yield a measure of the density of the fluid. In this aspect, a diffraction grating sensor as described above is provided in combination with an acoustic impedance sensor.

In one advantageous variation, the acoustic impedance sensor is also capable of obtaining data without requiring through transmission through the fluid. Such a sensor is described in commonly owned U.S. application Ser. No. 10/099,412 filed Mar. 15, 2002 and titled Self Calibrating System and Technique for Ultrasonic Determination of Fluid Properties, the disclosure of which is hereby incorporated by reference.

Turning now to FIG. 1, a system 20 for analyzing a property of fluid 25 and which can be used in conjunction with system 400 described above is depicted. Fluid 25 can be a gas, liquid, slurry, suspension, paste, emulsion and the like. In preferred forms, fluid 25 is substantially non gasseous and/or includes at least one liquid. In this form, fluid 25 might be, for example, a liquid, slurry, or suspension. In further preferred forms fluid 25 has a viscosity greater than about 0.5 cP and/or a density greater than about 0.3 g/cm$^3$.

Ultrasonic transducer 30 is acoustically coupled to a first surface 42 of a member 40 comprised of a solid material. In one example, transducer 30 is in direct contact with member 40. In other examples, one or more couplants might be used between transducer 30 and member 40, or they may be coupled as would otherwise occur to those skilled in the art. An opposed second surface 44 of member 40 is in contact with the fluid 25. A pulser 22 is electrically coupled to transducer 30 and is operable to deliver input stimulus signal to transducer 30 to cause transducer 30 to emit acoustic energy through solid member 40 and towards fluid 25. Transducer 30 is also operable to produce output signals in response to acoustic energy transmitted from member 40. A processing apparatus 22 including receiver 60, digitizer 70, and computer 80, is coupled to pulser 22 and to transducer 30. Processing apparatus 22 controls delivery of the transducer input signals, receives the output signals from transducer 30, and, as described more fully below, performs calculations to determine properties of fluid 25 as a function of the transducer output signals.

Figure 7:
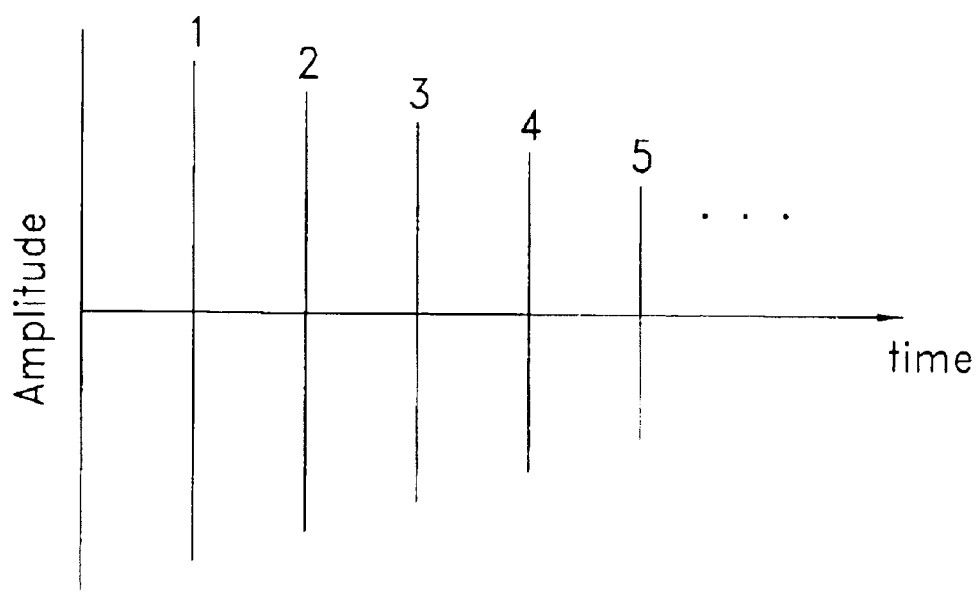
FIG. 7 is an exemplary plot of echo magnitude versus time illustrating echoes 1–5 of a representative diminishing series of echo amplitudes.

In operation, pulser 50 generates and delivers a short duration stimulus to transducer 30. Transducer 30 responds to the stimulus by emitting a longitudinal wave pulse of ultrasound into member 40. This ultrasonic pulse reflects between surfaces 44 and 42 producing a series of pulse echoes at transducer 30. This resulting echo series will be of successively diminishing echo amplitude because each successive echo will have reflected from the solid fluid interface at surface 44 one time more than the previous echo. An exemplary plot of echo magnitude versus time after the initial pulse, illustrating echoes 1–5 of a diminishing series of echoes, is shown in FIG. 7.

Transducer 30 responds to the echoes by producing an output signal proportional to the echo amplitude that is amplified by receiver 60, digitized by digitizer 70 and passed to computer 80. Computer 80 includes programming instructions encoded on fixed and/or removable memory devices 84, 86, respectively, to select a peak echo amplitude for the series echoes and to determine the average decay rate of the peak echo amplitudes with increasing echo number in the echo series. Alternatively, computer 80 can be at least partially hard wired with dedicated memory devices and configured to execute logic according to the present invention. Computer 80 is operatively coupled to display 82 to output selected information about fluid 25 integrated with transducer 30.

Preferably a number of echo amplitudes, for example 5 or more, spanning a range of echo numbers are used in computing the decay rate. In one preferred form, computer 80 is programmed to first compute the fast Fourier transform (FFT) of the digitized signal, converting it from the time domain to the frequency domain and then determine the peak amplitude at a selected frequency, where the frequency is selected to be, for example, the center frequency of transducer 30. In a still further preferred form, the process is repeated for a number of pulses from transducer 30, and the average decay rate of the peak echo amplitudes is determined for each repetition. A rolling average of the resulting set of average decay rates is then determined.

Figure 8:
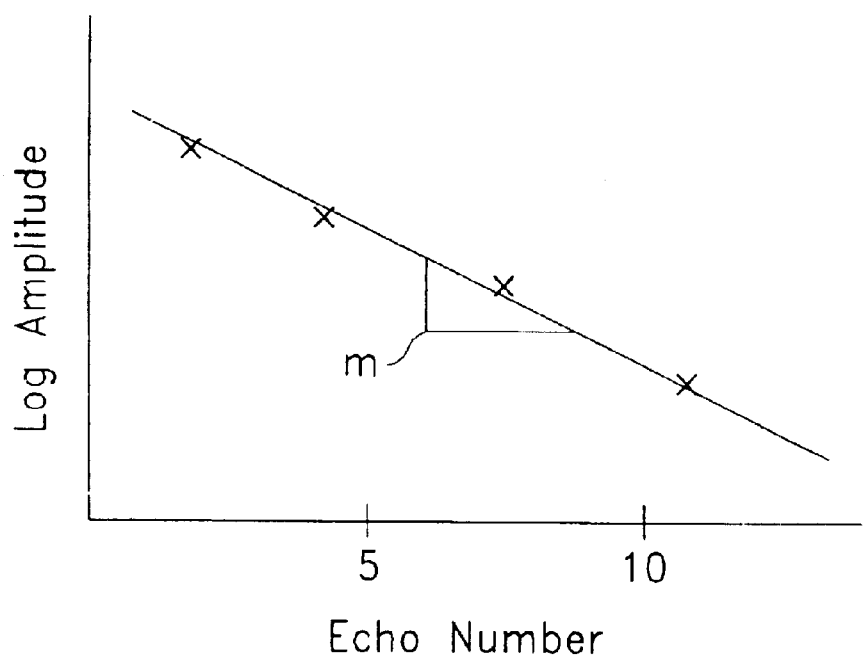
FIG. 8 is an exemplary plot of log echo amplitude versus echo number with a straight line fit to the exemplary data where m indicates the slope of the line.

The determined average decay rate can be expressed as the slope of the line of the natural log of echo amplitude versus echo number (mF). An exemplary plot of log echo amplitude versus echo number with a line fit to the exemplary data is shown in FIG. 8. Utilizing this expression of the average decay rate, computer 80 calculates the reflection coefficient for the fluid-solid interface (RCfluid) according to equation (1)

$$RCfluid/RCcalib = e^{(mF-mC)} \qquad (1)$$

where mC is the slope of the natural log of echo amplitude versus echo number determined by replacing the fluid 25 with a calibration fluid, and RCcalib is the calculated reflection coefficient for the fluid-solid interface when the fluid is the calibration fluid. The values for RCcalib and mC are stored in memory 84 and/or 86, and the value for RCcalib is calculated in advance according to equation (2)

$$RCcalib = (Zcalib - Zsolid)/(Zcalib + Zsolid) \qquad (2)$$

where Zcalib is the acoustic impedance of the calibration fluid and Zsolid is the acoustic impedance of the solid member 40.

Instead of calculating two slopes as given by equation (1), an equivalent processing technique is to divide the output from transducer 30 received for each echo by the corresponding value for the calibration fluid (i.e. water) to yield a normalized echo amplitude (NA) for each echo number. The slope of the plot of natural log of these normalized echo amplitudes versus echo number (mNA) is then used to calculate the ratio of the reflections coefficients by equation (1a):

$$RCfluid/RCcalib = e^{mNA} \qquad (1a)$$

As would be apparent to those of skill in the art, substitution of mNA for mF−mC in equation (1) is mathematically and theoretically equivalent, but by eliminating the subtraction of separate slopes, has the potential to minimize the propagation of rounding and measurement errors.

From the fluid specific reflection coefficient (RCfluid), computer 80 calculates the acoustic impedance of the fluid (Zfluid) according to equation (3)

$$Zfluid = Zsolid(1-RCfluid)/(1+RCfluid) \qquad (3)$$

where Zsolid is the acoustic impedance of the solid member 40.

From the acoustic impedance of the fluid (Zfluid), computer 80 calculates a physical property of the fluid. The density of the fluid (PF) is calculated according to equation (4)

$$\rho_F = Zfluid/Vfluid \qquad (4)$$

where Vfluid is the speed of the sound in the fluid. An indication of the fluid density is then produced on display 82.

Figure 2:
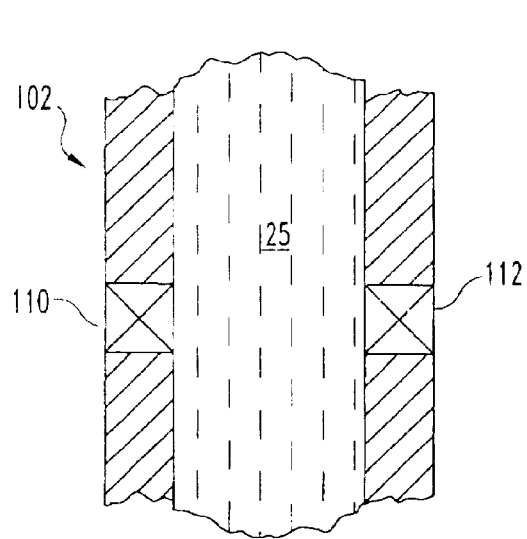
FIG. 2 is a schematic view of a device for performing an ultrasonic time-of-flight measurement on a fluid.
Figure 3:
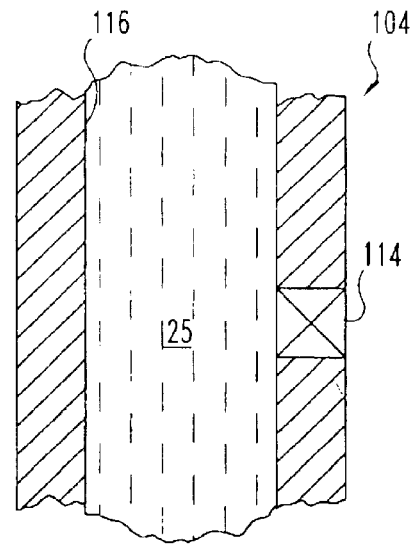
FIG. 3 is a schematic view of another device for performing an ultrasonic time-of-flight measurement on a fluid.

In one form, the speed of sound (Vfluid) is determined by performance of a time-of-flight measurement on the fluid. A time-of-flight measurement is accomplished by measuring the time it takes an ultrasound pulse to travel a known distance through the fluid 25. The speed of sound (Vfluid) is then determined by dividing the known distance by the determined transit time. FIGS. 2 and 3 schematically illustrate devices 102 and 104 for performing time-of-flight measurements that can form a portion of system 20. In the FIG. 2 embodiment, a pair of transducers 110, 112 are arranged in pitch-catch mode and measure the time it takes sound to travel from transducer 110 to transducer 112. In the FIG. 3 embodiment, a single transducer 114 is arranged relative to a surface 116 in pulse-echo mode for measuring the time it takes sound to travel from transducer 114 to surface 116 and back. Because the ultrasound travels through the fluid in a time-of-flight measurement, it is preferred to use a lower frequency of ultrasound in the time-of-flight measurement than in the echo measurement to minimize attenuation of ultrasound in the fluid during the time-of-flight measurement. In particular forms, the time-of-flight measurement is performed at a frequency below about 1 MHz.

In another form, the speed of sound is determined via ultrasonic diffraction grating spectroscopy as described above. As will be appreciated by those of skill in the art, the use of ultrasonic diffraction grating spectroscopy eliminates the need to perform a time of flight measurement and provides the ability to measure a value for speed of sound that does not require traversal of a section of the fluid.

Figure 4:
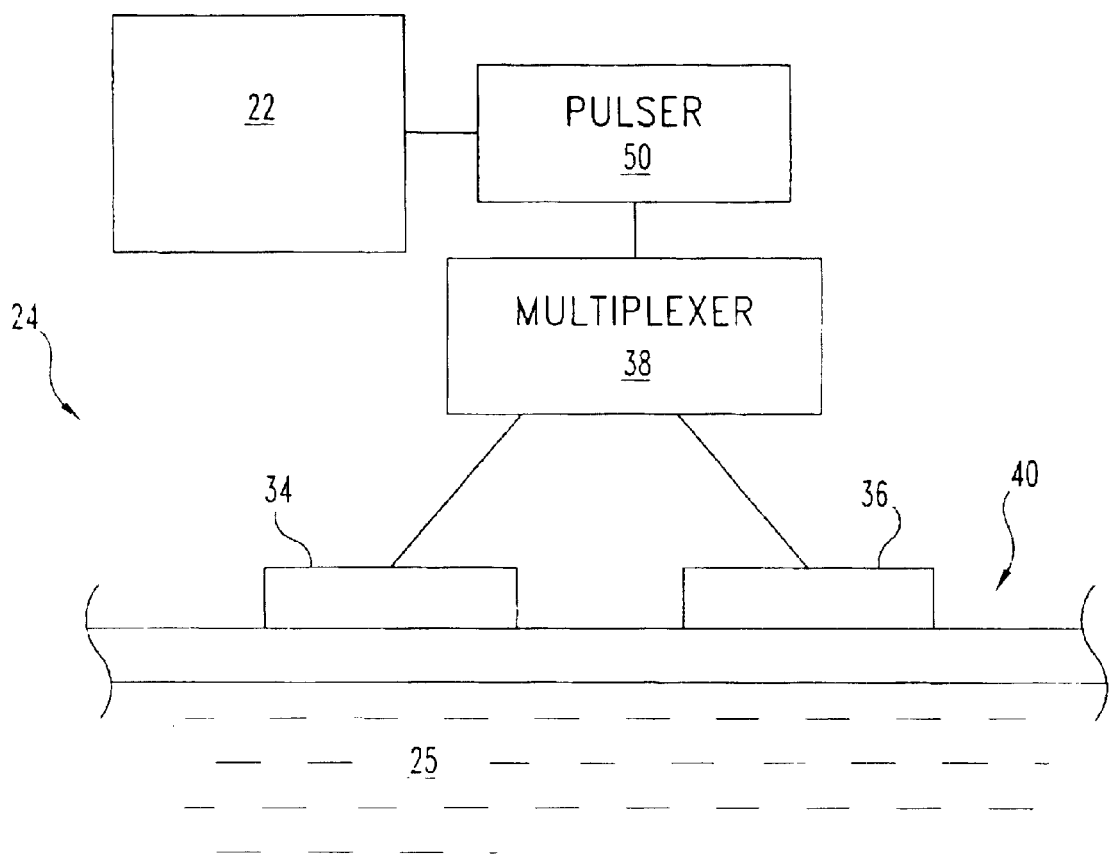
FIG. 4 is a diagrammatic view of a variation of the FIG. 1 system for determining fluid properties.

One variation of system 20 is depicted in FIG. 4. System 24 includes both a shear wave transducer 34 and a longitudinal wave transducer 36. Transducers 34 and 36 are each coupled to pulser 50 and processing apparatus 22 via a multiplexer 38. In this variation, processing apparatus 22 is programmed to simultaneously or sequentially cause shear waves and longitudinal waves to be reflected through member 40. Processing apparatus 22 is programmed to receive the output of longitudinal transducers 34 when longitudinal waves are being reflected through member 40 and to determine fluid density information as described above with respect to system 20. Alternatively, longitudinal wave transducer 34 can be omitted with fluid density determined by any other means known in the art.

Processing apparatus 22 is also programmed to determine one or more additional properties of the fluid utilizing the response of transducer 36 to the reflected shear waves in combination with the determined density information. The response from shear transducer 36 is process as described above with respect to transducer 30 to calculate the acoustic impedance of the fluid according to equations (1)–(3), where the values used in equation (1)–(3) and the determined acoustic impedance (Zfluid) appropriately correspond to values for shear waves.

In one preferred form, the additional properties determined from the shear wave acoustic impedance depend on the properties of the fluid being interrogated. The propagation of a shear waves in liquids is described in J. Blitz, Fundamentals of Ultrasonics, $2^{nd}$ Edition, Plenum Press, New York, 1967, pp.130–134, which is hereby incorporated by reference in its entirety. As described in Blitz, both the viscosity ($\eta$) and the shear modulus (G) are parameters in differential equations involving the rate of change of the shear strain, the pressure, and the pressure time dependence for shear wave propagation. The relaxation time ($\tau$) for liquids is defined as the viscosity ($\eta$) divided by the shear modulus (G). Where the relaxation time is small such that the terms involving G can be ignored, the viscosity of the fluid ($\eta$) is calculated in accordance with equation (5).

$$Zfluid = (\omega \rho_F \eta/2)^{0.5} \qquad (5)$$

where $\omega$ is the radial frequency of the shear wave and $\rho_F$ is the determined fluid density. Exemplary small relaxation times for this form include relaxation times less than about $10^{-9}$ and more preferably on the order of about $10^{-12}$. An equivalent formulation for determining fluid viscosity by combining equations (3) and (5) and substituting for Zsolid is given in equation (5a).

$$(\rho_F \eta)^{0.5} = \rho s \, c_{TS} \left(\frac{2}{\omega}\right)^{0.5} \left(\frac{1 - RCfluid}{1 + RCfluid}\right) \quad (5a)$$

where ρs is the density of the solid and $c_{TS}$ is the shear wave velocity in the solid.

For fluids 25 where the value of ωτ>>1, shear modulus (G) or the shear velocity in the fluid ($c_{tf}$) can be calculated according to equations (6) and (7).

$$Zfluid = (\rho_F G)^{0.5} \quad (6)$$

$$Zfluid = (\rho_F c_{tf}) \quad (7)$$

Exemplary values for ωτ according to this form include values greater than about 3 and more preferably greater than about 11.

In other forms or where these simplifications are not utilized, additional fluid properties can be determined by solving Blitz's differential equations numerically and/or by any means known in the art.

Figure 9:
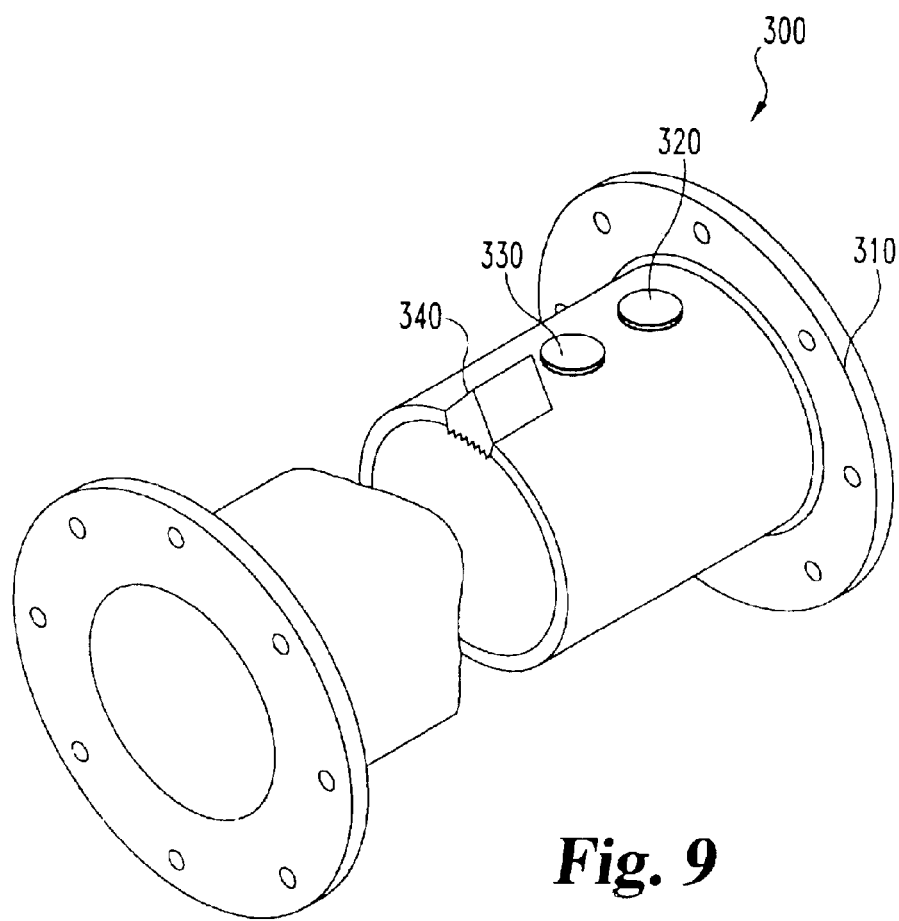
FIG. 9 is a perspective view of an acoustic system for determining fluid properties implemented as a spool piece that can be coupled to a process line. The acoustic system of FIG. 9 is a combination sensor that includes a pair of transducers for performing sensing based on multiple reflections from a fluid-solid interface and a pair of transducers for performing ultrasonic diffraction grating spectroscopy.
Figure 9A:
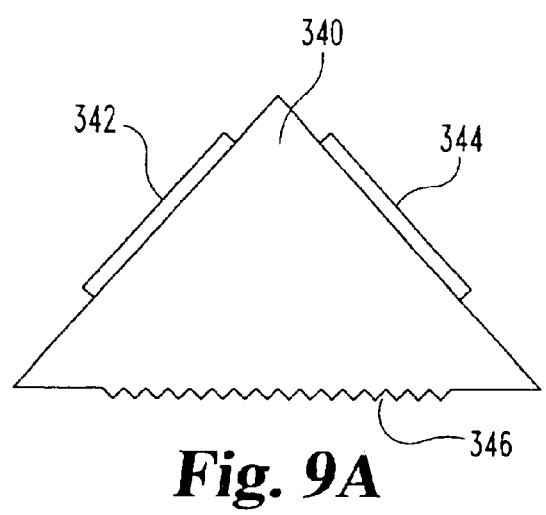
Figure 10:
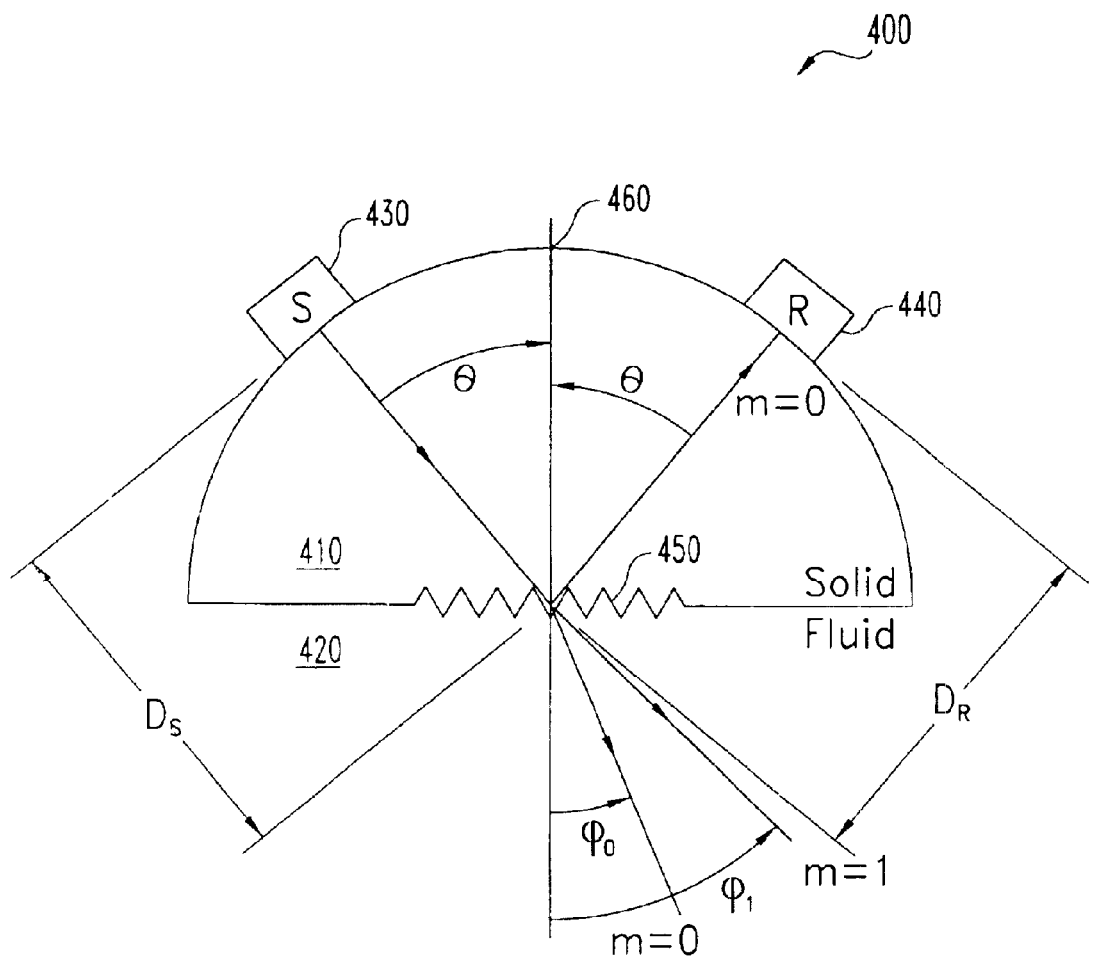
FIG. 10 is a schematic illustration of a system for detecting the reflection spectrum including the zero order diffraction.
Figure 11:
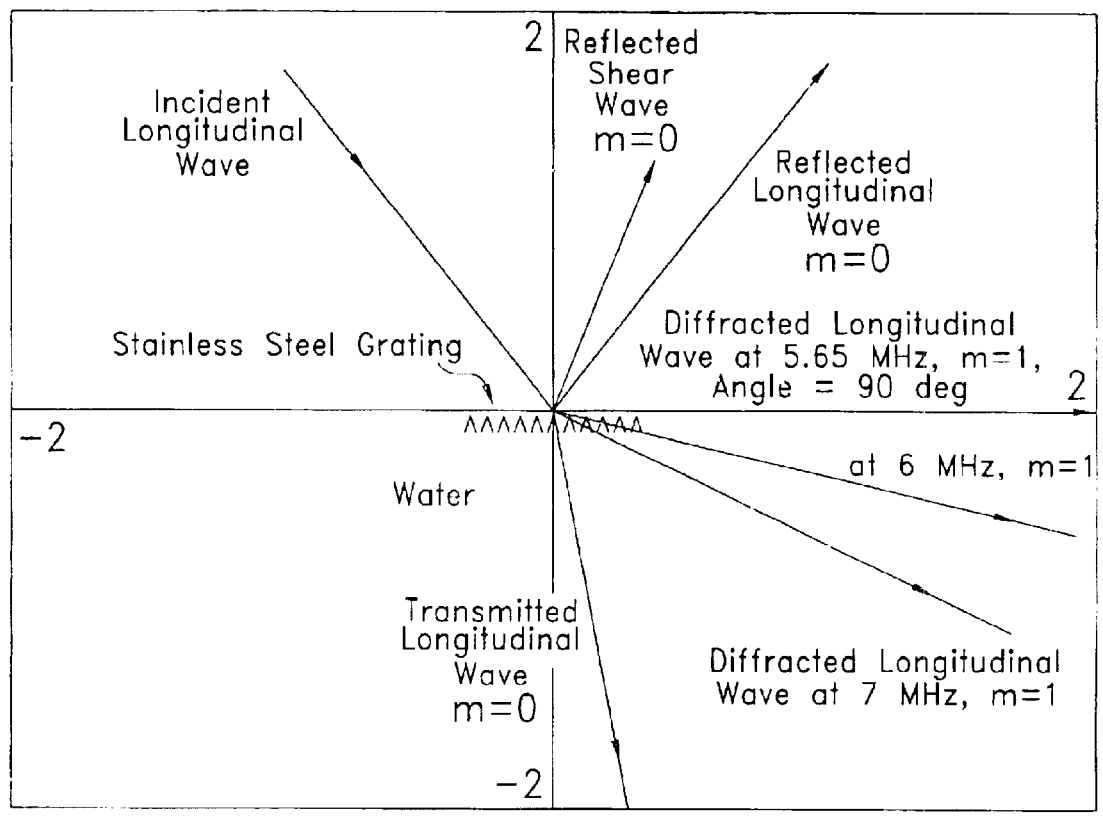
FIG. 11 is an exemplary schematic illustration of the relative location of reflected and transmitted zero order waves for a stainless steel water interface with a diffraction period of 300 $\mu$m and illustrating the frequency dependence of the relative orientation of the diffracted first order waves.

One application for the invention, depicted in FIGS. 9 and 9A, includes a fluid sensor system 300 that can be inserted in a pipeline and coupled to appropriate electronics to determine fluid properties in accordance with the present invention. System 300 includes a spool piece 310 that is adapted to be inserted in a section of a process pipeline which conveys a fluid in need of characterization. The spool piece 310 includes a shear wave transducer 320 and a longitudinal wave transducer 330. The transducers 320, 330 are configured to detect multiple reflections of an echo series as described above. The spool piece also includes a solid member 340 having a diffraction grating 346, a send transducer 342 and a receive transducer 344. The grating 346 is positioned to contact the fluid contents of the spool piece 310, and transducers 342, 344 are positioned to perform diffraction grating spectroscopy as described above. Each of the transducers 320, 330, 342, 344 are coupled to one or more computer(s) (not shown) or similar processing device (s) for performing the calculations described above for determining desired properties of the fluid such as speed of sound, acoustic impedance, density, and viscosity. Additional sensors can also be included in the spool piece 310 such as a thermocouple, pressure transducers, and/or a flow meter for measuring fluid temperature, pressure drop, and/or flow velocity.

Transducers useful for forming and receiving the ultrasound pulse echo series in practicing the present invention can operate in the range of about 0.5 to 20 MHz, more preferable between about 1 and 10 MHz, and most preferably about 5 MHz. In certain applications of the invention, the thickness T of member 40 will be predetermined, and depending on the wavelength of ultrasound in the member 40, the ratio of thickness T to wavelength could be significant, for example greater than about 0.05. As one example, it is contemplated that member 40 would be the existing wall of a stainless steel pipe or container about 0.15 inches thick. For at least some selected ultrasonic frequencies, the wavelength of ultrasound will be significant relative to the wall thickness.

Where the length of the pulse in the member 40 is a concern, a broadband ultrasound pulse can be used. Pulser 50 inputs a square wave or spike input to transducer 30, where the non-sinusoidal input has a duration less than the time it takes the transducer to perform a half cycle at the transdcuer center frequency (give by the inverse of the frequency of the transducer). The transducer 30 responds to this short input stimulus by emitting an ultrasonic pulse into member 40 of short duration, for example on the order of about 3–4 wavelengths in length. In this manner, the length of the ultrasound pulse in member 40 can be minimized and the echoes detected by transducer 30 can be readily resolved, because the potential for overlap is typically reduced.

In another form, because of the materials desired for solid member 40 and fluid 25, the acoustic impedance ratio Zsolid/Zfluid will be significant, for example, greater than about 5 or 10. In this form, the ultrasound pulse is preferably detected as it undergoes a large number of reflections between surfaces 42 and 44 of member 40, for example more than about 10 reflections, preferably about 15–20 reflections. The multiple reflections serve to amplify the effect of small changes in properties of fluid 25. This amplification occurs because the amplitude of the pulse is diminished in accordance with the reflection coefficient (RCfluid) with each successive reflection with surface 44. Also, because the higher echoes undergo more reflections with surface 44 and because the reflection coefficient (RCfluid) is a function of fluid properties, the effect of changes in these fluid properties are more pronounced in the higher echo numbers. Consequently, in one form of the invention, it is preferred that at least some of the higher number echoes are used in computing the decay rate.

In further forms, where reduction of the adverse effects of divergence and/or attenuation is of concern, selection of transducer 30 and member 40 dimensions and properties can be of particular interest. For example, the near field can be considered the region immediately in front of an ultrasonic transducer where the sound beam is does not diverge and signal loss is at a minimum. The near field length (Nf) for an ultrasonic transducer can be approximated by equation (8)

$$Nf = 0.25 D^2 / \lambda \quad (8)$$

where λ is the wavelength of the ultrasound in the medium (equal to local speed of sound divided by the frequency) and D is a dimension of the transducer face 32 associated with the member 40. For circular transducers, D will be the diameter of the face 32 whereas for rectangular transducers D is selected to be the larger length dimension of the rectangle for purposes of locating an approximate end to the near field. In one form of the invention, the near field of the transducer 30 is selected to encompass one or more of the reflections used to calculate the decay rate. In a preferred form, a plurality of the echoes used to calculate the decay rate are within the near field length estimated by equation (8). In a further preferred form, the majority of the echoes used to calculate the decay rate are within this length. Most preferably, substantially all of the echoes are within this length.

From an examination of equation (8) one possibility for increasing the near field length is to increase the frequency of the ultrasound. However, there is a practical limit to the effectiveness of this approach, at least because losses due to attenuation of the ultrasound generally increase with increasing frequency. The near field length is therefore preferably maintained at a desired relative length by adjusting the ratio of the size of transducer size D to thickness T. Increasing the transducer size D increases the near field length whereas decreasing T decreases the pathlength of the echoes, allowing more echoes to be detected inside a given near field length. It is to be understood that the pathlength for each echo is the distance the pulse travels for each reflection (2T) times the echo number (the first echo has a pathlength of 2T, the second 4T, the third 6T, etc.). While any ratio can be utilized as would occur to those of skill in the art, in one form of the invention the ratio of D/T is preferably greater than about one. In other forms, the ratio D/T is about 2 or above.

An advantage is realized by using the decay rate of the echo amplitudes (represented by the two slopes mF and mC) in determining fluid properties. It has been found that, unlike the absolute magnitude of individual echo amplitudes, the slope of echo amplitude versus echo number is substantially independent of characteristics of the ultrasound pulse used to create the echoes. This independence was confirmed experimentally utilizing a 1 inch diameter longitudinal transducer in contact with a 0.25 inch thick stainless steel plate. The transducer operated at 5 MHz and the opposed surface of the plate was in contact with water.

In one set of experiments, the width of a −300 volt square wave input to the transducer was varied. It was found that, while the absolute value of the $6^{th}$ echo amplitude changed by about 21% when the width of the voltage input was changed from 102 nanoseconds to 68 nanoseconds, the slope of the natural log of the FFT amplitude versus echo number changed by less than 0.1%.

In a second set of experiments the voltage of a 100 nanosecond square wave input was changed from −300 volts to −50 volts and the slopes of the amplitude versus echo number log plots were determined. While the magnitude of the voltage input was decreased by a factor of six, the calculated slope of the log of amplitude versus echo number changed by less than 2%.

As described above with respect to FIGS. 9 and 9A, in one application the transducer 30 and solid member 40 are provided as a spool piece that is fixed in place in a pipeline. In other applications, preexisting pipe or container walls as utilized as member 40, and transducer 30 is configured as a clamp-on sensor that can be retrofit to existing equipment and/or readily moved from one pipeline or container to the next. In these latter applications, where preexisting walls provide member 40, the use of the slope of the log of echo amplitude versus echo number is particularly advantageous.

Figure 5:
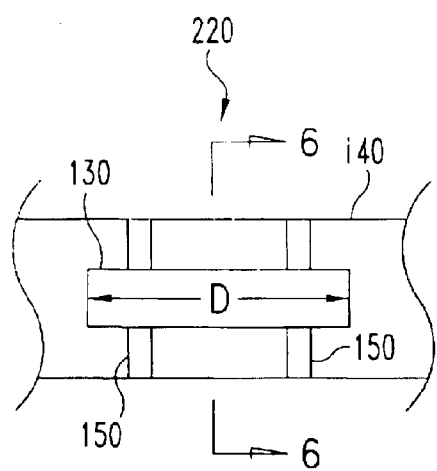
FIG. 5 is a side view of a clamp on sensor attached to a pipeline.
Figure 6:
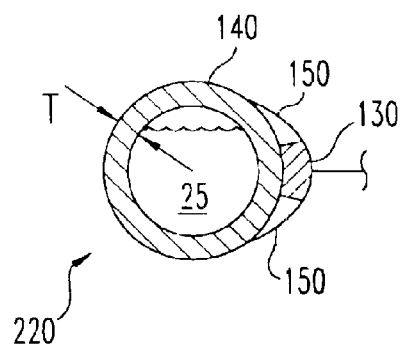
FIG. 6 is a sectional view of the FIG. 5 sensor.

Turning now to FIG. 5, an exemplary clamp on sensor 220 for use on a pipeline is illustrated. Sensor 220 includes an ultrasonic transducer 130 which is used in place of transducer 30 in system 20. Transducer 130 is curved to correspond to the outer diameter of pipe 140, and transducer 130 is held to the outside surface of a pipe 140 with clamps 150 that extend around pipe. Transducer 130 is generally rectangular with its longer dimension D oriented parallel to the flow direction of the pipe 140. This longer length D is preferably greater than the pipe wall thickness T for the reasons described above. As one example, a curved rectangular transducer 0.4 inches by 1 inch could be chosen for a stainless steel pipe with an outside diameter of 2.375 inches and a wall thickness of 0.15 inches. An acoustic couplant, not shown, is optionally provided between transducer 130 and pipe 140. It is to be understood that the strength of any particular signal from transducer 130 might depend on, for example, the pressure exerted by clamps 150, which in turn could depend on additional factors, such as the care with which transducer 130 is attached to pipe 140. However, the slope of the log of echo amplitude versus echo number would be relatively independent of variables such as connection pressure, leading to increased accuracy of the device.

In use, clamp on sensor 220 can be calibrated with any fluid present in pipe 140. If the pipe is empty, air can be the calibration fluid. If the pipeline is conveying a process fluid, the process fluid can be the calibration fluid. Subsequent changes in the process fluid can then be quantitatively or qualitatively determined according to the present invention.

It is to be understood that, while in a retrofit system such as system 220, the existing material of the pipe or container wall dictates the choice of solid material used, a wide variety of materials can serve as the member 40 as would occur to those of skill in the art. Exemplary materials for solid member 40 include aluminum, stainless steel, fused quartz, and plastics. Preferably member 40 is non-porous is does not absorb fluid 25. In particular applications, such as food processing and the transport of toxic material, stainless steel or other non-corrosive materials are preferred materials for solid member 40.

In a further variation, data transmission between computer 80 and transducer 30 can be achieved wirelessly by provision of appropriate wireless communication devices.

It is also to be understood that another embodiment is a unique technique to determine fluid properties wherein an ultrasonic transducer 30 is provided on a surface 42 of a solid member 40 having an opposed second surface 44 in contact with the fluid 25. This technique can include delivering an ultrasonic pulse through the solid member, detecting a multiplicity of pulse echoes caused by reflections of the ultrasonic pulse between the solid-fluid interface and the transducer-solid interface, and determining the decay rate of the detected echo amplitude as a function of echo number. The determined decay rate is compared to a calibrated decay rate to determine an acoustic property of the fluid. In one form, the speed of ultrasound in the solid is also determined and the fluid viscosity and/or the fluid density is determined as a function of the speed of ultrasound and the determined acoustic property.

Another form of the invention is a system for determining a property of a fluid comprising a diffraction grating in contact with the fluid and formed on a first member; an interrogation device providing ultrasound that passes through at least a portion of the first member and is incident on the diffraction grating at an angle of incidence; a detector for capturing a reflection spectrum from the diffraction grating when the ultrasound is incident on the diffraction grating, the reflection spectrum including a diffraction order equal to zero; and a processing device receiving an output of the detector for determining a value corresponding to a property of the fluid based upon the reflection spectrum. The processing device can be operable to determine the value by selecting a wavelength corresponding to a peak in the reflection spectrum. The property of the fluid can be speed of sound in the fluid. The interrogation device can include a transducer face in acoustic contact with the first member. The transducer face can be spaced from the diffraction grating a distance at least about equal to $D^2/(4\lambda)$ where D is the smallest dimension of the transducer face and $\lambda$ is the wavelength of the ultrasound in the solid material. The grating can include at least 20 grooves with a period between about 50 $\mu$m and about 500 $\mu$m. The grating can include grooves with a triangular cross section. The angle of incidence can be between about 25 and about 50°. The first member can be stainless steel. There can also be a second member comprised of solid material and having first and second opposed surfaces with a transducer in acoustic contact with the first surface and the second surface in contact with the fluid. The transducer in acoustic contact with the first surface of the second member can be coupled to a processing device operable to determine a value corresponding to acoustic impedance of the liquid from a decay rate of ultrasound reflected between the first and second surfaces of the second member.

Still another form is a method for determining a property of a fluid comprising interrogating a diffraction grating in contact with the fluid with ultrasound at an angle of incidence by passing the ultrasound through a member comprised of solid material and having the diffraction grating having a grating period formed on a face thereof, receiving a response to the interrogating wherein the response includes a reflection spectrum of ultrasound reflected at a predetermined angle relative to the normal of the diffraction grating; and determining first value corresponding to a property of the fluid by selecting a peak in the reflection spectrum. Determining the value can include comparing the value to a value for a calibration sample. The interrogation can be performed with a transducer having a face spaced from the grating a distance at least about equal to $D^2/(4\lambda)$ where D is the smallest dimension of the transducer face and $\lambda$ is the wavelength of the ultrasound in the solid material. A second value corresponding to density of the fluid can be determined from the first value and a third value corresponding to acoustic impedance. This third value can be determined by reflecting an ultrasound pulse a multiplicity of times between a pair of opposed surfaces one of which is in contact with the fluid.

While the invention has been illustrated and described in detail in the drawings and foregoing description, the same is to be considered illustrative and not restrictive in character, it being understood that only the preferred embodiment has been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least one", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A system for determining a property of a fluid comprising:
    a diffraction grating having a grating period in contact with the fluid and formed on a first member comprised of solid material;
    an interrogation device providing ultrasound that passes through at least a portion of the first member and is incident on the diffraction grating at an angle of incidence;
    a detector for capturing a reflection spectrum from the diffraction grating when the ultrasound is incident on the diffraction grating, the reflection spectrum including a diffraction order equal to zero; and
    a processing device receiving an output of the detector for determining a value corresponding to a property of the fluid based upon the reflection spectrum.

2. The system of claim 1 wherein the processing device is operable to determine the value by selecting a wavelength corresponding to a peak in the reflection spectrum.

3. The system of claim 2 wherein the property of the fluid is speed of sound in the fluid.

4. The system of claim 1 wherein the interrogation device includes a transducer face in acoustic contact with the first member.

5. The system of claim 4 wherein the transducer face is spaced from the diffraction grating a distance at least about equal to $D^2/(4\lambda)$ where D is the smallest dimension of the transducer face and $\lambda$ is the wavelength of the ultrasound in the solid material.

6. The system of claim 4 wherein the grating includes at least 20 grooves on the grating and the grating period is between about 50 µm and about 500 µm.

7. The system of claim 6 wherein the angle of incidence is between about 25 and about 50°.

8. The system of claim 4 wherein the gratings have a triangular cross section.

9. The system of claim 1 wherein the first member includes stainless steel.

10. The system of claim 1 further comprising a second member comprised of solid material having first and second opposed surfaces with a transducer in acoustic contact with the first surface and the second surface in contact with the fluid.

11. The system of claim 10 wherein the transducer in acoustic contact with the first surface of the second member is coupled to a processing device operable to determine a value corresponding to acoustic impedance of the liquid from a decay rate of ultrasound reflected between the first and second surfaces of the second member.

12. The system of claim 10 wherein at least one of the first and second members include stainless steel.

13. A method for determining a property of a fluid comprising:
    interrogating a diffraction grating in contact with the fluid with ultrasound at an angle of incidence by passing the ultrasound through a member comprised of solid material and having the diffraction grating having a grating period formed on a face thereof,
    receiving a response to the interrogating wherein the response includes a reflection spectrum of ultrasound reflected at a predetermined angle relative to the normal of the diffraction grating; and
    determining first value corresponding to a property of the fluid by selecting a peak in the reflection spectrum.

14. The method of claim 13 wherein determining the value includes comparing the value to a value for a calibration sample.

15. The method of claim 13 wherein the interrogation is performed with a transducer having a face spaced from the grating a distance at least about equal to $D^2/(4\lambda)$ where D is the smallest dimension of the transducer face and $\lambda$ is the wavelength of the ultrasound in the solid material.

16. The method of claim 13 further comprising determining a second value corresponding to density of the fluid from the first value and a third value corresponding to acoustic impedance.

17. The method of claim 16 further comprising determining the third value by reflecting an ultrasound pulse a multiplicity of times between a pair of opposed surfaces one of which is in contact with the fluid.

18. The method of claim 13 wherein the response includes a diffraction order equal to zero.

19. The method of claim 13 wherein the predetermined angle is equal to the angle of incidence.

20. A method for determining speed of sound in a fluid comprising:
    providing a diffraction grating having a grating period formed on a member comprising solid material;
    providing ultrasound through the member and incident on the diffraction grating at an angle of incidence;
    capturing reflections from the diffraction grating while the diffraction grating is in contact with the fluid and the ultrasound is incident on the diffraction grating; and determining speed of sound by selecting a frequency corresponding to a peak in the spectrum of the captured ultrasound.

21. The method of claim 20 wherein the angle of incidence is between 15° and 50°.

22. The method of claim 20 wherein the diffraction grating has a grating period between about 5 and 500 µm.

23. The method of claim 20 wherein the diffraction grating includes a plurality of grooves.

24. The method of claim 23 wherein the ultrasound is incident on at least a portion of about 30 of the grooves.

25. The method of claim 20 wherein the captured reflections from the diffraction grating include a diffraction order equal to zero.

26. A system for characterizing a fluid comprising:
- a fluid conduit defining an interior and an exterior;
- a first member comprising solid material;
- a diffraction grating having a grating period formed on the first member and facing the interior of the conduit;
- at least first and second ultrasonic transducers in acoustic contact with the first member and operable to interrogate the diffraction grating with ultrasound and to receive a response to the interrogating;
- a second member comprised of solid material and having first and second opposed surfaces with the second surface facing the interior of the conduit;
- a third transducer in acoustic contact with the first surface of the second member and operable to deliver ultrasound for reflection between the first surface and the second surfaces to provide an ultrasound echo series at the third transducer;
- a processing device operable to determine a value corresponding to at least one property of a fluid in the interior of the conduit from at least one of the response from the first or second transducer and the response from the third transducer when a fluid is in the interior of the conduit.

* * * * *